United States Patent [19]

Dika et al.

[11] 4,456,623

[45] * Jun. 26, 1984

[54] RUMINANT ANIMAL FEED AND METHOD OF MAKING SAME

[75] Inventors: John A. Dika, Kewaunee; Fredrick W. Juengst, Jr., Green Bay, both of Wis.

[73] Assignee: Calor Agriculture Research, Inc., Kewaunee, Wis.

[ * ] Notice: The portion of the term of this patent subsequent to Jun. 8, 1999 has been disclaimed.

[21] Appl. No.: 480,234

[22] Filed: Mar. 30, 1983

[51] Int. Cl.$^3$ ............................................... A23K 1/22
[52] U.S. Cl. ........................................ 426/69; 426/74; 426/807
[58] Field of Search ..................... 426/69, 807, 72, 74

[56] References Cited

U.S. PATENT DOCUMENTS 4,333,956  6/1982  Juengst et al. ..................... 426/69

OTHER PUBLICATIONS

Webb, "Byproducts from Milk" Avi Publishing Co., 1970, pp. 58-61.
Hanulo et al., Powdered Feed from Corn, Chemical Abstracts, vol. 84 (1976), Abstract No. 149585m.
Hawley, "Condensed Chemical Dictionary" Van Nostrand Reinhold Publishers, 1982, p. 187.

*Primary Examiner*—R. B. Penland
*Attorney, Agent, or Firm*—Cushman, Darby & Cushman

[57] ABSTRACT

A process of producing a ruminant animal feed by mixing calcium ammonium lactate sediment derived by precipitation from fermented ammoniated condensed whey, with calcium sulfate and drying the mixture in contact with air.

4 Claims, 3 Drawing Figures

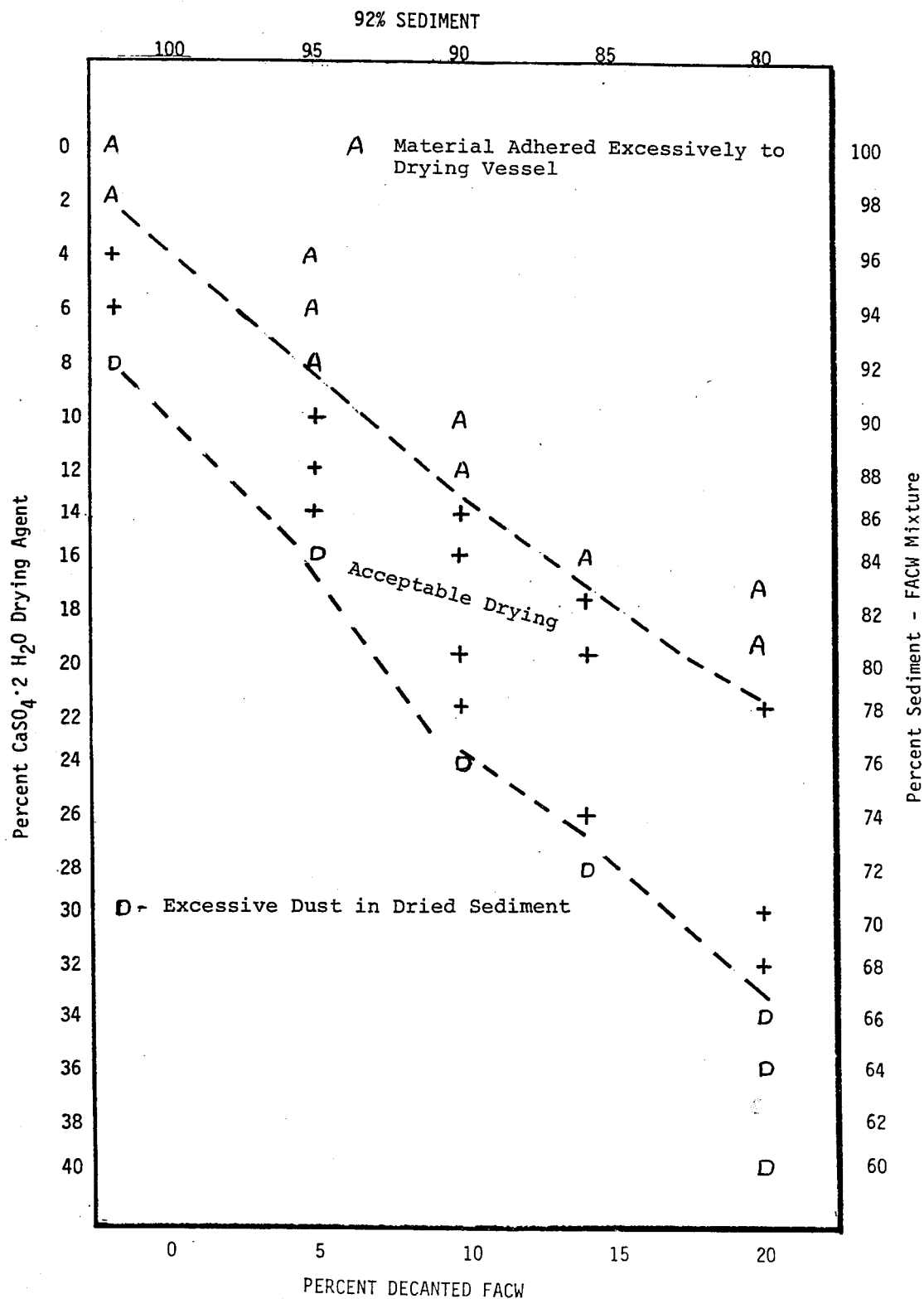

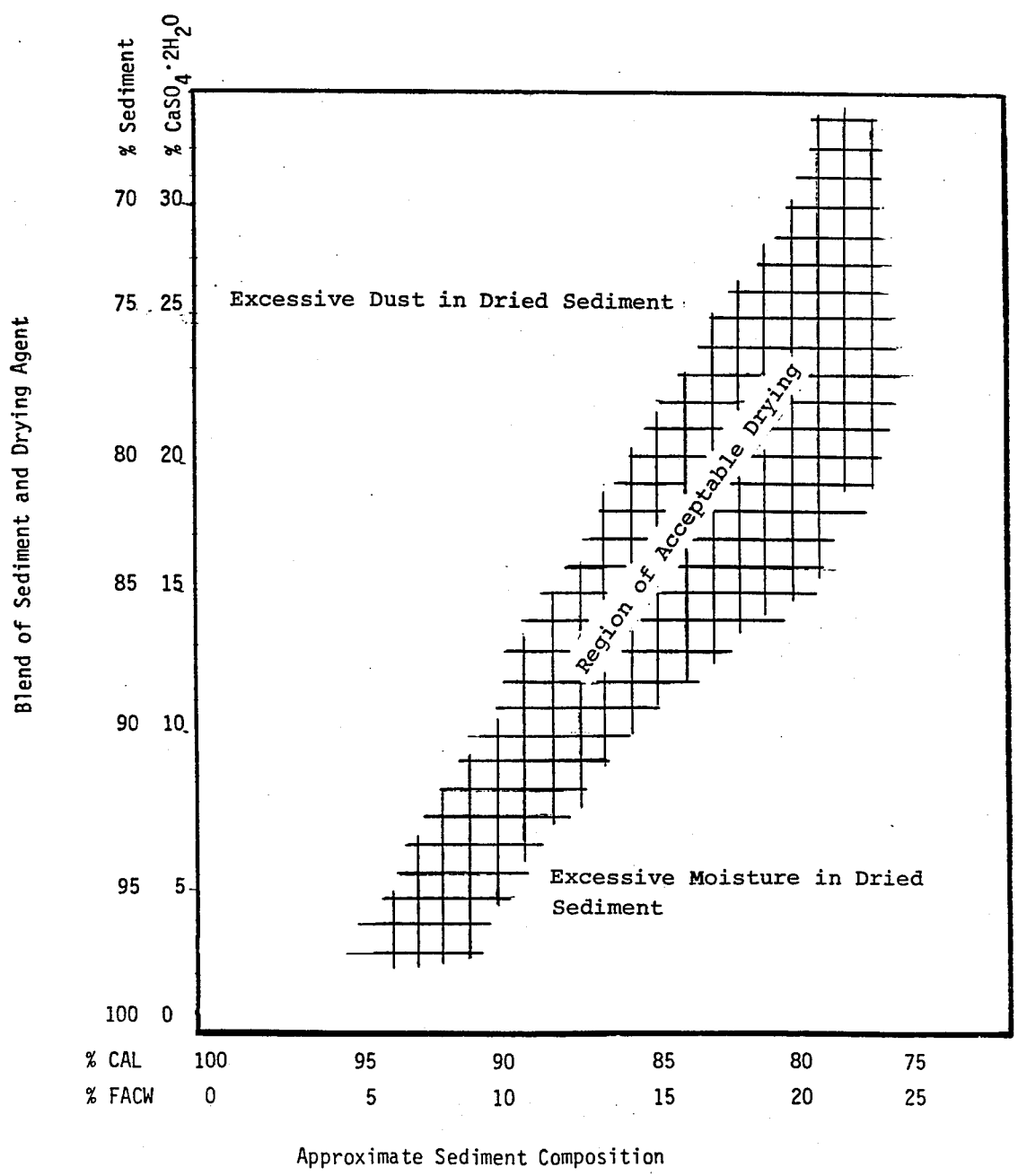

RUMINANT ANIMAL FEED AND METHOD OF MAKING SAME

The present invention relates to a ruminant animal feed, and a method of making the same. More specifically, it relates to a method of producing a solid, granular form of calcium ammonium lactate (hereinafter referred to as "CAL").

BACKGROUND OF THE INVENTION

CAL is a crystalline substance which is formed in the manufacture of fermented ammoniated condensed whey (hereinafter referred to as "FACW"). Further information on both CAL and FACW may be obtained from U.S. patent of Juengst et al. U.S. Pat. No. 4,333,956 granted June 8, 1982. The disclosure of that patent relating to these substances is incorporated herein by reference.

Under certain conditions, CAL separates from FACW and crystalline CAL can be collected. However, the CAL collected is in the form of a sediment usually, containing small amounts of FACW. Therefore, it is not a free-flowing powder. The handling of the CAL sediment is therefore difficult, increasing its cost and limiting the ways in which it can be put to use.

SUMMARY OF THE INVENTION

The present invention provides a method for converting CAL sediment, derived from FACW, into a free-flowing solid material. Briefly, the process consists of mixing CAL sediment with calcium sulfate and air drying the mixture.

BRIEF DESCRIPTION OF FIGURES OF DRAWING

In the drawings:

FIGS. 2 and 3 are graphs tabulating data with respect to quantities of calcium sulfate to be used in relation to the composition of the feed.

DETAILED DESCRIPTION OF THE INVENTION

Figure 1:
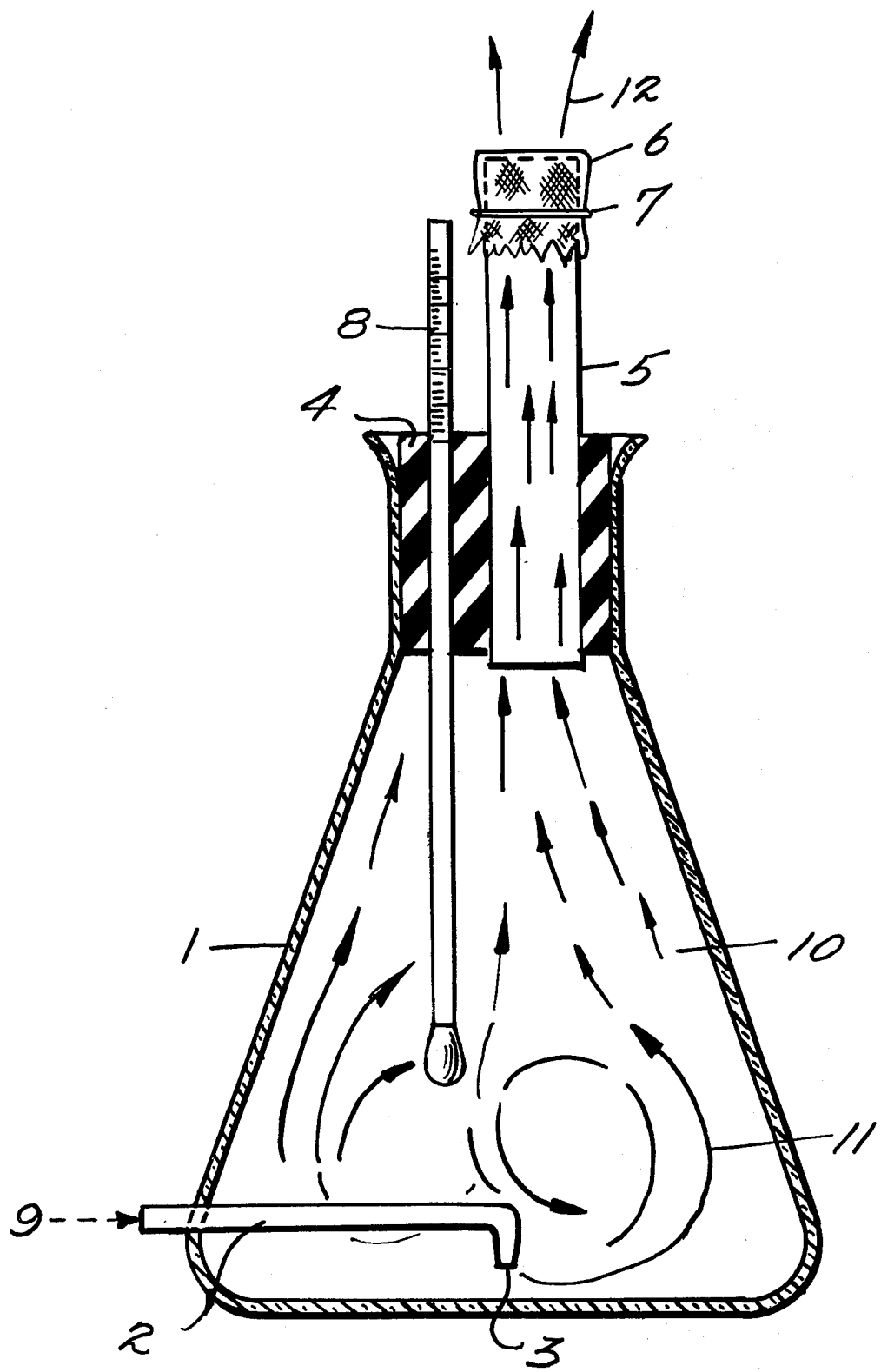
FIG. 1 is a side elevation view of a laboratory apparatus useful for practice of the process of the invention.

The raw material for the practice of the present invention is CAL sediment derived from FACW. Usually the FACW is obtained as a hot liquid after it has been concentrated by evaporating water, using heat. The FACW is cooled to allow formation of CAL crystals to be completed. Then the mixture is decanted, for example in a continuous centrifuge such as the Sharples P-3400 Super-D-Canter. The product should be decanted promptly after the crystals have formed, as the recovery of crystals by decantation is more efficient when the product is fresh. For example, a sample stored for two days gave a higher recovery of CAL solids than a three month old sample. The product obtained at this stage is a semi-dry crystalline material.

The second raw material used in the present invention is calcium sulfate. Preferably, the product is calcium sulfate dihydrate or calcium sulfate hemihydrate. The hemihydrate was found to be somewhat more effective, in that the rate of drying was somewhat higher. For instance, in an experiment with comparable feeds and drying conditions, the hemihydrate produced a dry product in 5–6 minutes whereas the dihydrate required 7–8 minutes. Preferably the salt should be in the form of a granular or finely divided material. Other potential drying materials have been evaluated, including calcium chloride, calcium carbonate, dicalcium phosphate, soluble starch and shredded cellulose, but none was found to be as effective as calcium sulfate.

The amount of calcium sulfate utilized varies in accordance with the nature of the CAL sediment. In general, the amount used is about 2–30% of the total amount of mixture, and it depends upon the amount of FACW in the sediment. The exact amount to be used for a particular CAL sediment can be determined by a simple experiment, using the apparatus illustrated in FIG. 1. Mixtures of the sediment with various amounts of calcium salt are dried in that apparatus or a similar apparatus. Incomplete drying can be detected by adherance of the feed to the walls of the drying vessel. Excessive drying can be detected by a massive buildup of particles on the filter at the exit of the drying vessel, or by fine particles blowing through the filter. In general, acceptable levels for calcium sulfate dihydrate have been found to correspond to the following equations. A minimum amount of calcium sulfate, as the dihydrate, is given by the equation % $CaSO_4 = 1.12 \,(100 - \% \,CAL) - 6$. A reasonable maximum is given by the equation % $CaSO_4 = 1.40 \,(100 - \% \,CAL) - 6$.

More detailed information on the appropriate amount of calcium sulfate to be used can be derived from FIGS. 2 and 3. FIG. 2 is a graph recording the results of experiments in which various mixtures were dried. The mixtures contained a sediment which in turn contained 92% CAL (balance FACW). This sediment was then mixed with various amounts of decanted FACW to provide mixtures for drying. Across the top of the graph the percentage of CAL sediment (containing 92% CAL) is indicated whereas across the bottom of the graph the corresponding amounts of FACW added to the mixtures are indicated. On the vertical axes, the percentages of calcium sulfate dihydrate mixed with the sediment/FACW mixtures is indicated at the left, and at the right there is given the percentage of the sediment-FACW mixture which was combined with the calcium sulfate. The two lines plotted along the graph indicate upper and lower limits on the amount of calcium sulfate found to be acceptable. The amounts of calcium sulfate corresponding to the area between the lines gave acceptable drying. Higher amounts, indicated by the area below the lines in the graph, gave excessive dusting whereas smaller amounts of calcium sulfate caused the material to adhere excessively to the drying vessel.

FIG. 3 is another graph, based upon the same experiments. In this case, the horizontal axis indicates the proportion of CAL and FACW (in total) and the vertical axis indicates the proportion of sediment and calcium sulfate in the mixtures which were dried. The hatched area in the center of the graph indicates appropriate amounts of calcium sulfate to be used, in accordance with the composition of the material being dried.

Various forms of apparatus can be used to dry the mixtures of CAL sediment and calcium sulfate. For example, a fluidized bed or other conventional air drying equipment may be used. The product may also be dried to simply spreading it out on a flat surface and letting it stand, for example overnight.

The air used to dry the apparatus is conveniently at room temperature. Temperatures up to 30° C., or a little higher, have been found to be satisfactory. At temperatures of 40° C. or above, it was found that the product tended to form into clumps and not dry evenly.

A suitable laboratory apparatus for carrying out the invention is illustrated in FIG. 1. This apparatus was found to be suitable for drying 25 gram quantities of sediment. In the Figure, reference numeral 1 indicates a 500 ml Erlenmeyer flask having an air inlet tube 2 extending horizontally through the lower portion of the side of the flask. At the inner end of the air inlet tube 2, the tube is bent downwardly and narrowed to give a 2 mm diameter orifice 3. The top of the flask is sealed by a rubber stopper 4, and an exit tube 5 is inserted through the stopper, having an internal diameter of 10 mm and a height of 200 mm. At the upper end of the exit tube, there is a fine gauze 6 covering the exit, held in place by a rubberband 7. A thermometer 8 also is inserted through the rubber stopper 4, to observe the temperature of the air flowing through the flask. The numeral 9 indicates the inward flow of air to the flask, at a rate of 12 liters per minute. The arrows 10 indicate the air flow through the flask and the arrows 11 indicate the circulation of the sediment as it is being dried.

In a series of experiments, 25 gram samples of CAL sediment were mixed with various potential drying agents, and the results of the experiments are recorded in Table 1. In this case, the sediment contained 93% CAL and 7% FACW liquid. The drying air was at 23° C. The flask was weighed as the experiment continued, for 10 minutes, to determine the amount of liquid which had been removed by evaporation, and this is recorded as the percentage of mass lost in Table 1.

TABLE 1

Percent of Mixture Evaporated

| Drying Agents | % Drying Agent | Minutes | | | | | | | | | |
|---|---|---|---|---|---|---|---|---|---|---|---|
| | | 1 | 2 | 3 | 4 | 5 | 6 | 7 | 8 | 9 | 10 |
| Calcium Chloride Dihydrate | 0 | 1.6 | 2.4 | 3.2 | 3.6 | 3.6 | 4.0 | 3.6 | 4.4 | 4.4 | 4.8 |
| | 2 | 1.2 | 2.0 | 2.8 | 3.6 | 4.0 | 4.4 | 4.4 | 4.8 | 4.8 | 4.8 |
| | 4 | 1.2 | 2.0 | 2.4 | 2.8 | 3.2 | 3.6 | 4.0 | 4.0 | 4.0 | 4.4 |
| | 6 | 1.6 | 2.0 | 2.4 | 3.2 | 4.0 | 4.0 | 4.0 | 4.4 | 4.4 | 4.4 |
| | 8 | 0.8 | 1.6 | 2.4 | 2.8 | 2.8 | 3.2 | 3.6 | 3.6 | 3.6 | 3.6 |
| Calcium Sulfate Dihydrate | 0 | 0.8 | 1.2 | 2.0 | 2.4 | 2.8 | 2.8 | 3.2 | 3.6 | 3.6 | 4.0 |
| | 2 | 0.8 | 1.6 | 2.0 | 2.8 | 3.6 | 4.0 | 4.4 | 4.4 | 4.4 | 4.4 |
| | 4 | 2.0 | 2.4 | 3.6 | 4.4 | 4.8 | 5.2 | 5.2 | 5.2 | 5.6 | 5.6 |
| | 6 | 1.2 | 2.0 | 3.2 | 4.0 | 4.4 | 4.8 | 5.2 | 5.6 | 5.6 | 5.6 |
| | 8 | 1.6 | 2.4 | 3.2 | 4.0 | 4.4 | 4.8 | 5.2 | 5.6 | 5.6 | 6.0 |
| Calcium Carbonate | 0 | 0.8 | 1.6 | 2.0 | 2.4 | 2.8 | 3.2 | 3.2 | 3.6 | 4.0 | 4.0 |
| | 2 | 1.2 | 1.8 | 2.4 | 3.2 | 3.6 | 4.0 | 4.2 | 4.4 | 4.8 | 4.8 |
| | 4 | 1.2 | 1.8 | 2.4 | 2.8 | 3.6 | 4.0 | 4.2 | 4.4 | 4.4 | 4.4 |
| | 6 | 0.8 | 1.6 | 2.8 | 3.2 | 3.6 | 4.0 | 4.4 | 4.6 | 4.6 | 4.8 |
| | 8 | 0.8 | 1.6 | 2.2 | 2.8 | 3.2 | 3.6 | 3.6 | 4.4 | 4.8 | 4.8 |
| Dicalcium Phosphate | 0 | 0.8 | 1.4 | 1.8 | 2.2 | 2.8 | 3.0 | 3.4 | 3.6 | 4.0 | 4.0 |
| | 2 | 0.8 | 1.4 | 1.8 | 2.2 | 2.8 | 3.0 | 3.4 | 3.4 | 3.8 | 3.8 |
| | 4 | 1.0 | 1.6 | 1.8 | 2.2 | 2.8 | 3.0 | 3.4 | 3.6 | 3.6 | 4.0 |
| | 6 | 1.0 | 1.6 | 2.0 | 2.4 | 2.8 | 3.0 | 3.4 | 3.4 | 3.6 | 3.8 |
| | 8 | 0.8 | 1.4 | 2.0 | 2.4 | 2.8 | 3.2 | 3.2 | 3.6 | 3.8 | 4.0 |
| Soluble Starch Powder | 0 | 0.8 | 1.4 | 1.8 | 2.2 | 2.8 | 3.0 | 3.4 | 3.6 | 4.0 | 4.0 |
| | 2 | 1.2 | 2.0 | 2.4 | 2.8 | 3.2 | 3.6 | 4.0 | 4.0 | 4.0 | 4.2 |
| | 4 | 1.2 | 1.2 | 2.0 | 2.4 | 3.0 | 3.2 | 3.6 | 4.0 | 4.0 | 4.0 |
| | 6 | 1.2 | 1.8 | 2.6 | 3.2 | 3.4 | 4.4 | 4.6 | 4.8 | 4.8 | 5.2 |
| | 8 | 1.2 | 1.8 | 2.4 | 3.2 | 3.8 | 4.0 | 4.8 | 4.8 | 5.2 | 5.2 |
| Cellulose | 0 | 0.8 | 1.6 | 2.2 | 2.6 | 3.2 | 3.2 | 3.6 | 3.8 | 4.0 | 4.0 |
| | 2 | 0.8 | 1.0 | 2.4 | 3.2 | 3.6 | 3.6 | 3.8 | 4.2 | 4.4 | 4.8 |
| | 4 | 1.2 | 1.8 | 2.6 | 3.0 | 3.4 | 3.8 | 4.0 | 4.2 | 4.6 | 4.6 |
| | 6 | 1.0 | 1.8 | 2.6 | 3.4 | 3.6 | 3.8 | 4.0 | 4.0 | 4.4 | 4.6 |
| | 8 | 1.2 | 2.0 | 2.4 | 3.2 | 3.4 | 3.6 | 3.8 | 3.8 | 4.4 | 4.6 |

The properties of the sediment obtained after 10 minutes of air drying and 23° C. is given in Table 2.

TABLE 2

PROPERTIES OF DRIED SEDIMENT PRODUCTS
Properties of Sediment Products
After 10 Minutes of Air Drying at 23° C.

| Drying Agent | Percent Drying Agent | Sticky To The Touch | Compacted Under Pressure | Adhered To Drying Vessel | Balled Excessively | Smelled of Ammonia | Contained Dust or Powder Particles |
|---|---|---|---|---|---|---|---|
| Calcium Chloride Dihydrate | 0 | + | + | − | − | − | − |
| | 2 | + | + | − | − | − | − |
| | 4 | + | − | − | − | − | − |
| | 6 | − | − | − | − | − | − |
| | 8 | − | − | − | − | − | − |
| Calcium Sulfate Dihydrate | 0 | + | + | − | − | − | − |
| | 2 | + | + | − | − | − | − |
| | 4 | − | − | − | − | − | − |
| | 6 | − | − | − | − | − | − |
| | 8 | − | − | − | − | − | − |
| Calcium Carbonate | 0 | + | + | + | − | − | − |
| | 2 | + | + | + | − | − | − |
| | 4 | + | + | + | − | − | − |
| | 6 | + | + | − | − | + | − |
| | 8 | − | + | − | − | − | − |
| Dicalcium Phosphate | 0 | + | + | + | − | − | − |
| | 2 | + | + | + | − | − | − |
| | 4 | + | + | + | − | − | − |
| | 6 | + | + | + | − | − | − |
| | 8 | + | + | + | − | − | − |
| Soluble Starch Powder | 0 | + | + | + | − | − | − |
| | 2 | + | + | + | − | − | − |
| | 4 | + | + | + | − | − | − |
| | 6 | + | + | + | − | − | − |
| | 8 | + | + | + | − | − | − |
| Cellulose | 0 | + | + | + | − | − | − |
| | 2 | + | + | + | − | − | − |
| | 4 | + | + | + | − | − | − |
| | 6 | + | + | + | − | − | − |
| | 8 | + | + | + | − | − | − |

The composition of the product obtained using 4% calcium sulfate in the foregoing experiment is as follows:

| Constituent | Percent |
| --- | --- |
| Solids | 98 Est. |
| Total Nitrogen | 6.18 (38.6% CPE) |
| Ammonia Nitrogen | 5.95 (37.2% CPE from NPN) |
| Lactic Acid | 60.2 |
| Calcium | 7.98 |
| Sulfur | 0.57 Est. |

The product is useful as a nitrogen supplement for ruminant animals on high energy rations. The following is a brief description of a trial which was conducted using CAL sediment, that is the raw material used in accordance with the present invention. The product of the present invention can be used in essentially the same way, making an appropriate adjustment for the amount of sulfur introduced with the CAL.

Composition of CAL used in the trial was 8.6% Ca, 6.3% N, 74.4% lactic acid and 11.1% water. To determine the palatability of the benefit derived from supplementing corn silage with CAL, two trials were conducted. In trial 1, 18 steers (9 per pen) were fed increasing levels of CAL, (0.36, 0.40, 0.46, 0.50, 76 and 1.01 kg) in complete rations. For an additional 2 days, steers were offered CAL free choice separate from the complete ration. In trial 2, 32 steers (1 per pen) were fed cornsilage ad libitum and 1% of their dry matter as ground corn. Two of the pens received a negative control ration (9% CP) and the other two were supplemented with CAL to raise CP to 12%. When CAL was mixed in the complete ration in trial 1, total dry matter intakes were increased 12.3% from raising CAL intake from 0.36 to 0.46 kg; but they were markedly depressed at 1.01 kg per day. However, when CAL was offered free choice, steers ate 1.07 kg per day and total dry matter intakes were 30% higher than when CAL was added in the complete ration at 1.01 kg per day. In trial 2, daily feed intakes (kg/day) were slightly lower for the ration supplemented with CAL, but average daily gains exceeded the negative control group by 33.5% (0.93 vs 1.26 kg). Less feed was also required per unit gain when CAL was fed (6.34 vs 4.54). These results show that CAL can be effectively utilized as a nitrogen supplement for ruminants on high energy rations. Moreover, the material was palatable when fed free choice.

The foregoing description includes several specific embodiments. However, no limitation thereto is intended, the full scope of the invention being defined in the appended claims.

What is claimed is:

1. A process for the manufacture of a dried calcium ammonium lactate product which comprises forming a mixture of calcium ammonium lactate sediment said sediment containing calcium ammonium lactate in mixture with fermented ammonated condensed whey and an amount of calcium sulfate effective to produce said dried product and drying the mixture in contact with air at a temperature below 40° C.

2. A process as set forth in claim 1 in which the calcium sulfate is calcium sulfate dihydrate.

3. A process as set forth in claim 1 in which the calcium sulfate is calcium sulfate hemihydrate.

4. A process as set forth in claim 1 in which the mixture is dried by blowing air through a drying vessel in which the mixture is suspended.

* * * * *